United States Patent
Silber (10) Patent No.: US 11,464,317 B2
(45) Date of Patent: Oct. 11, 2022

(54) APPLICATOR DEVICE

(71) Applicant: Omeia SA, Cadempino (CH)

(72) Inventor: Gert Silber, Ponte Capriasca (CH)

(73) Assignee: OMEIA SA, Cadempino (CH)

( * ) Notice: Subject to any disclaimer, the term of this patent is extended or adjusted under 35 U.S.C. 154(b) by 310 days.

(21) Appl. No.: 16/624,783

(22) PCT Filed: Jun. 19, 2018

(86) PCT No.: PCT/EP2018/066209
§ 371 (c)(1),
(2) Date: Dec. 19, 2019

(87) PCT Pub. No.: WO2018/234286
PCT Pub. Date: Dec. 27, 2018

(65) Prior Publication Data
US 2020/0138169 A1    May 7, 2020

(30) Foreign Application Priority Data

Jun. 20, 2017   (WO) ................. PCT/EP2017/065099

(51) Int. Cl.
*A61F 13/40*     (2006.01)
*A47L 13/17*     (2006.01)
(Continued)

(52) U.S. Cl.
CPC ........... *A45D 37/00* (2013.01); *A45D 33/005* (2013.01); *A45D 40/00* (2013.01); *A61M 35/006* (2013.01);
(Continued)

(58) Field of Classification Search
CPC ...... A45D 37/00; A45D 33/005; A45D 40/00; A45D 2200/1018; A45D 2200/1036;
(Continued)

(56) References Cited

U.S. PATENT DOCUMENTS 3,240,326 A    3/1966   Miller
4,696,393 A    9/1987   Laipply
(Continued)

FOREIGN PATENT DOCUMENTS

JP    S57-043723 A    3/1982

OTHER PUBLICATIONS

International Search Report (ISR), dated Jul. 23, 2018, from corresponding International Application No. PCT/EP2018/066209.
(Continued)

*Primary Examiner* — David J Walczak
(74) *Attorney, Agent, or Firm* — Nixon & Vanderhye (57) ABSTRACT

An applicator device includes a top and a bottom layer of a flexible material tightly connected at their borders. An edge constitutes a grip zone to handle the applicator. Parallel weakening lines in each layer define an application section and closely surround a pad of a material capable to retain an agent or an elevation constituting a confinement structure for an agent. The superposition of weakening line and border of agent carrying material or the elevation constituting a part of the confinement structure avoids a contact of the flexible material with the surface to be treated as the carrying material layer or the confinement structure serve as a spacer.

(Continued)

As a consequence, the applicator is suited to be used on highly sensitive surfaces like skin or mucosa.

19 Claims, 4 Drawing Sheets

(51) Int. Cl.
    *A45D 37/00*     (2006.01)
    *A45D 40/00*     (2006.01)
    *A45D 33/00*     (2006.01)

(52) U.S. Cl.
    CPC ............... *A45D 2200/1018* (2013.01); *A45D 2200/1036* (2013.01); *A47L 13/17* (2013.01)

(58) Field of Classification Search
    CPC .......... A45D 34/00; A45D 2200/1009; A61M 35/006; A61M 35/00; A61M 35/003; B65D 47/42; B65D 47/44; B65D 47/36; A47K 7/00; A47K 7/02; A47L 13/16
    USPC ..... 401/132, 133, 261–264; 15/244.1, 244.3, 15/104.92, 104.93
    See application file for complete search history.

(56) References Cited

U.S. PATENT DOCUMENTS

| | | | | |
|---|---|---|---|---|
| 5,254,109 A | * | 10/1993 | Smith | ............... A61F 15/001 401/132 |
| 5,460,620 A | * | 10/1995 | Smith | ............... A61K 8/0208 604/290 |
| 9,254,027 B2 | | 2/2016 | Emery | |
| 2003/0213724 A1 | | 11/2003 | Dobler | |

OTHER PUBLICATIONS

Written Opinion of the International Searching Authority (ISA), dated Jul. 23, 2018, from corresponding International Application No. PCT/EP2018/066209.

International preliminary report on patentability, dated Dec. 24, 2019, from corresponding International Application No. PCT/EP2018/066209.

Office Action issued in Japanese Patent Application No. 2019-571508 dated Mar. 16, 2022.

\* cited by examiner

FIG. 15 though the applicator layer, which requires a non-impervious applicator layer and a sufficient pressure on the device to urge the agent through the applicator layer.

APPLICATOR DEVICE

BACKGROUND OF THE INVENTION

Field of the Invention

The present patent application relates to an applicator device according to the preamble of claim 1. It further relates to methods for producing the device and uses of the device.

Applicator devices as intended by the present invention are flexible, merely two-dimensional means which serve to apply a substance to a surface. The devices may be used by a person or by a machine, e.g. a robot. Preferably, a contact between the hand of the person (analogously: gripping means of a machine or manipulating device, e.g. a manipulator in a glove-box), the surface and the substance is avoided. Reasons may be cosmetic, hygienic, technical, or simply psychological. The application may be on sensible biological surfaces, like the skin of a person or an animal in general, or a delicate technical surface.

Description of the Related Art

U.S. Pat. No. 9,254,027 discloses an applicator device constituted by a substantially sheet-shaped carrier. The applicator comprises a flexible sheet. It bears on the applicator side a layer of a not-impervious material. The not-impervious layer covers only part of the total surface and in particular leaves the perimeter of the flexible sheet uncovered. Between the flexible sheet and the not-impervious layer, a quantity of a deodorant powder is encased. Like wings the sheet is folded on itself to create a pouch, and held closed by a closure tab.

Typically, the fold acting as a grip or backbone is held, and the walls of the pouch are spread like wings to be applied on a surface. In moving on the surface, the powder penetrates the not-impervious layer and is dispersed on the surface.

U.S. Pat. No. 3,240,326 (Miller) discloses an applicator having wings to be spread, where each wing is enclosed individually in that the protecting sheet is folded back between the wings in the closed state. The pad can be opened, i.e. the wings be spread, in pushing a finger into this inner fold, and after opening, peripheral parts of the protecting sheet together with the part covering the active surface are ripped off. By folding the protective sheet back between the wings, the active surface is covered, and the finger inserted for opening does not get in contact with the active surface or the agent.

Yet, the weakening lines are applied the way that there is excess protective layer material around the active surface, and additional protective sheet material is required for folding back between the wings.

A problem not considered by the prior art consists in that the flexible carrier sheet, more particularly its border, gets in contact with the surface under treatment. As the carrier sheet is designed to impart stability and other mechanical properties needed that the device can be handled, it may contaminate, irritate, scratch or otherwise mechanically impair the delicate surface.

Another issue in the mentioned prior art is that the active substance is enclosed between applicator layer and carrier sheet. Hence, the periphery of the applicator layer has to be attached to the carrier sheet for a tight enclosure. In use, the active substance has to penetrate the applicator layer which requires a non-impervious applicator layer and a sufficient pressure on the device to urge the agent through the applicator layer.

Furthermore, at first the "dry" applicator layer gets in contact with the surface, as the agent appears only on its surface during use of the applicator device.

BRIEF SUMMARY OF THE INVENTION

Therefore, it is an object of the present invention to propose a device wherein the probability is increased that only the applicator layer gets in contact with a surface to be treated.

Such an applicator device is defined by claim 1. The further claims define preferred embodiments, a method for producing the device and uses of the device.

Accordingly, the applicator device has a main weakening line narrowly surrounding an applicator portion so that other parts, in particular of the carrier sheet, outside the applicator portion can be ripped off.

The carrier sheet is partitioned into two adjacent sections or wings, so that after folding the wings on each other, the applicator portion constitutes a pouch surrounded by a sealing portion. Within the pouch, applicator pads, preferably one on each wall of the pouch (i.e. each wing), and/or substantially line shaped elevations or ribs are present defining the area intended to be applied to a surface, i.e. the applicator portion. The main weakening lines of the two carrier sheet sections are preferably substantially mirror-symmetrical so that they may be exactly superposed. With the area to be applied extending up to the weakening lines, the border of the carrier sheet after ripping off along the weakening line is about identical with the border of the applicator portion, so that the pads or delimiting ribs may act as spacer and keep the carrier sheet off the surface to be treated. "about identical" is understood to comprise the situation that the pads protrude to a small extent beyond the weakening lines, or the weakening lines extend interior of the pads to a small degree, or some smaller distance down to exactly coincident.

Furthermore, strip-shaped grip sections arranged at the border of the wings are designed to be folded and affixed to each other by gluing, welding, crimping or other methods known per se, in order to constitute a backbone or grip section.

In use, the grip section may be gripped and the excess portion of the carrier sheet is ripped off. The wings now freely extending from the grip section may be readily spread once the applicator device is applied to a surface to be treated.

The applicator pads may consist of any suitable material for the surface to be treated, particularly in order to avoid damaging or otherwise negatively influencing the surface. Preferred are non-woven, sponge-like materials, foams and the like. A pad needs to have at least an effective thickness, respectively a line shaped elevation or rib needs to have at least an effective height.

Preferably, an agent is provided on the surface of the applicator layer, like a cream, liquid, ointment, skin care product, peeling composition, pharmaceutically active substances or formulation, powder, polishing material or the like. In general, any matter needed to be applied to a surface to be treated may be present on the applicator and shall be understood as such an agent, including pure materials and mixtures.

Delicate or easily irritable skin areas may be areas of thin or sensible skin. A most sensible skin area is the perivulvar region. Another sensible region is near the eye.

The applied substance may serve to modify the surface (polishing, cleaning, activating for ulterior treatment, or in the contrary passivation), to care, or to support a healing process (application of liquids, creams, powder, pharmaceutical or cosmetic preparations for topic application).

BRIEF DESCRIPTION OF THE DRAWINGS

The invention will be explained in detail by preferred embodiments and in referring to the Figures. In the Figures, thicknesses are exaggerated for the sake of illustration and do not reflect either the actual thickness ratios of the layers.

DETAILED DESCRIPTION OF THE PREFERRED EMBODIMENTS

Figure 2:
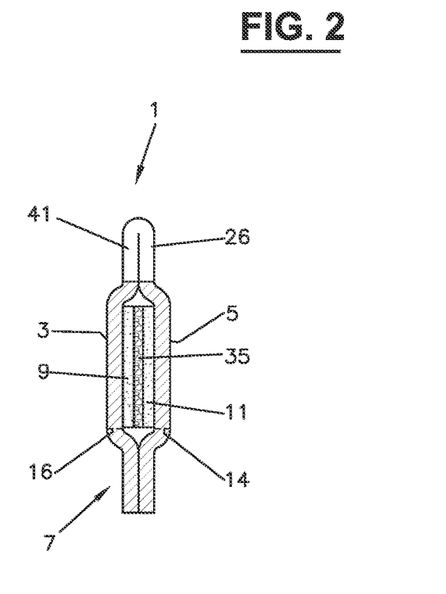
FIG. 2 section of the applicator device according to II-II in FIG. 1.

The applicator device or applicator 1 comprises two carrier sheet sections or wings 3, 5 of a carrier sheet 7, namely an upper wing 3 (top layer) and a lower wing 5 (bottom layer) as shown in FIG. 2. On each wing 3, 5, a pad 9, 11 of a suitable, non-irritating material is arranged.

The applicator pads 9, 11 are attached to the respective wing 3, 5 by a suitable technique, e.g. gluing, crimping, or welding.

Figure 3:
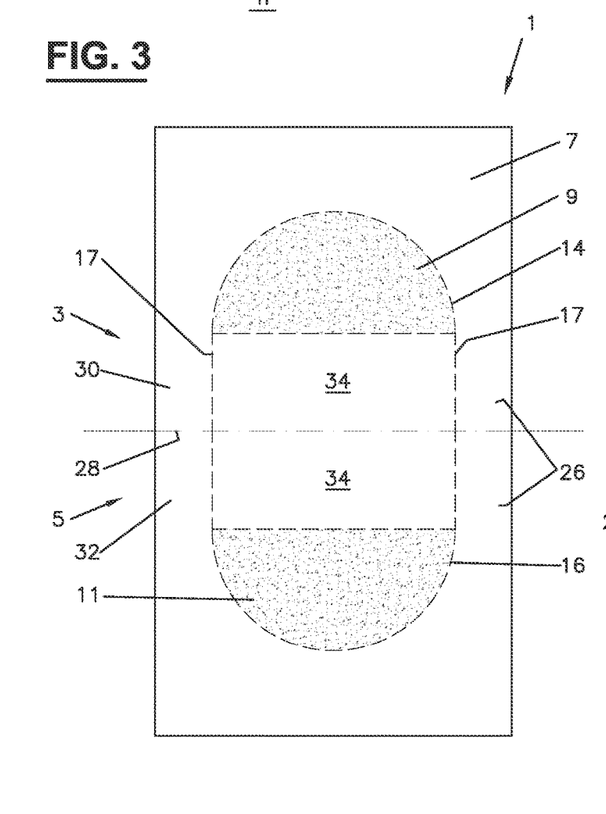
FIG. 3 top view on applicator device before folding and sealing.

The applicator pads 9, 11 are surrounded by main weakening lines 14, 16 in the wings 3, 5. The weakening lines 14, 16 are extended by terminal weakening lines 17 through the grip sections 30, 32 constituting the middle section 26 of the carrier sheet 7. The main weakening lines 14, 16 together with the extensions or secondary weakening lines serve to separate the exterior part 22 of the carrier sheet 7 from the part bearing the pads 9, 11 and the grip sections 30, 32 which, when folded on and affixed to each other, constitute a handle or grip of the applicator device. In some embodiments, the applicator sections are comprised of the applicator pads 9, 11 which provide a volume (9, 11) of a material carrying the agent.

Figure 1:
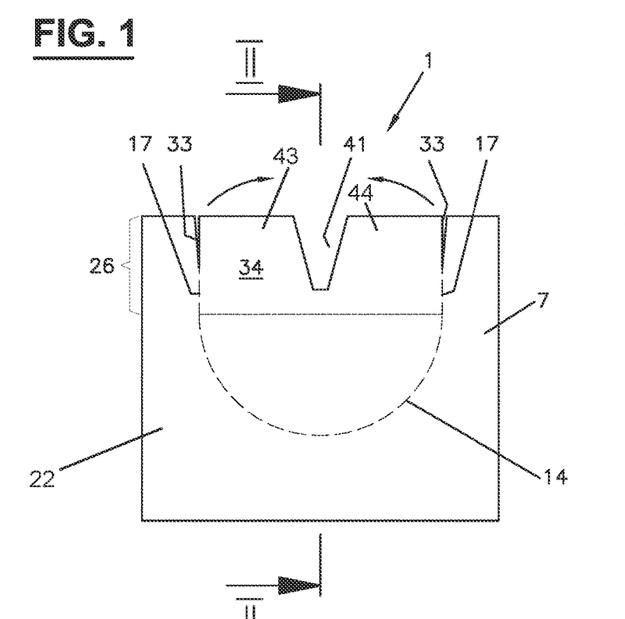
FIG. 1 Top view on applicator device.

The main weakening lines 14, 16 follow quite exactly the contour of the pads 9, 11 or are even slightly recessed so that the peripheries of the pads are minimally exterior of the area defined by the weakening line 14 respective 16. Thereby, it is avoided that the carrier sheet, in particular a boundary thereof, gets in contact with a surface on which the applicator device 1 is used while maintaining a support and mechanical stabilisation of the pads by the backing carrier sheet 7. Upper wing 3 and lower wing 5 of carrier sheet 7 are separated by a folding line 28. Above and below folding line 28 in FIG. 3, stripe-shaped handle sections 30, 32 of upper wing 3 and lower wing 5 are provided. Upper wing 3 and lower wing 5 are in its entirety mirror-symmetric with respect to folding line 28, so that the two wings may be superposed by folding at folding line 28 (cf. FIGS. 1, 2) and in the superposed state, pads 9, 11 and weakening line 14, 16 are exactly positioned over its counterpart.

Before folding, or before sealing the applicator device 1, an agent 35 to be applied to a surface by the applicator 1 is put or dispersed on or into one or both pads 9, 11. The applicator device is sealed, thereby tight enclosing pads 9, 11 and the agent 35 in a closed pouch, by connecting upper and lower wing 3, 5 in the areas surrounding the pads 9, 11 and the grip sections 30, 32 by a suitable manner which may be welding, gluing, crimping, or combinations thereof, for example. For welding, the material of the carrier sheet may be a thermoplastic polymer material or is covered with a thermoplastic material which is capable to be welding in the areas to be welded at least.

In order to facilitate the opening of the applicator device 1, cuts 33 are provided at the ends of weakening line extensions 17.

For use, the part of the carrier sheet 7 exterior to the pads 9, 11 is ripped off along the weakening lines 14, 16 so that a work portion remains constituted substantially of the remaining part 34 of grip sections 30, 32 by which the applicator 1 can be held during the opening action and the ulterior application, and of the parts covered by the pads 9, 11. The latter are now hingedly connected to the joined grip sections part 34. In particular, a user may hold the applicator 1 by the grip part 34, press the applicator 1 onto a surface 36 (arrow 38 in FIG. 4) whereby the pads 9, 11 are spread (arrows 40 in FIG. 4). For treating the surface 36 (applying agent and possibly impregnating in or dispensing on the surface) applicator 1 is moved appropriately on the surface 36.

Figure 4:
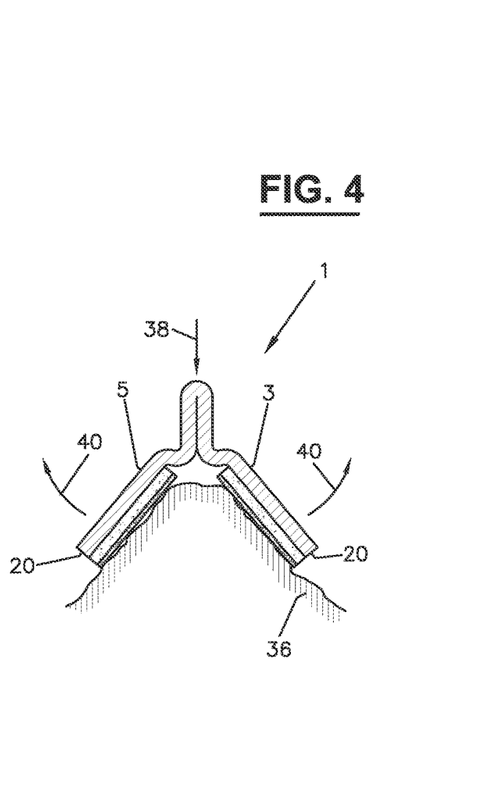
FIG. 4 schematic illustration of the use of the applicator device as a section analogous to FIG. 2.

Notably, FIG. 4 shows that the pads 9, 11 exceed by a small degree the weakening lines 14, 16. If the pads 9, 11 extend beyond the weakening lines, the risk is further significantly reduced that the carrier sheet 7 or its rim constituted by the weakening lines may get in contact with the surface to be treated. By experience, the weakening line is preferably at least 1 mm set back with respect to the rim of the pad. More specifically, the distance to the rim of the pads 9, 11 is 1 to 3 mm for a diameter of the pads of 3 to 10 cm, and 2 to 5 mm for pads of diameter of 10 cm and more. For this purpose, "diameter" designates the largest distance between two points on the rim of a pad 9, 11. Hence, for the pads of the example, the diameter is the diameter of the circle surrounding the shape of the pads.

Figure 11:
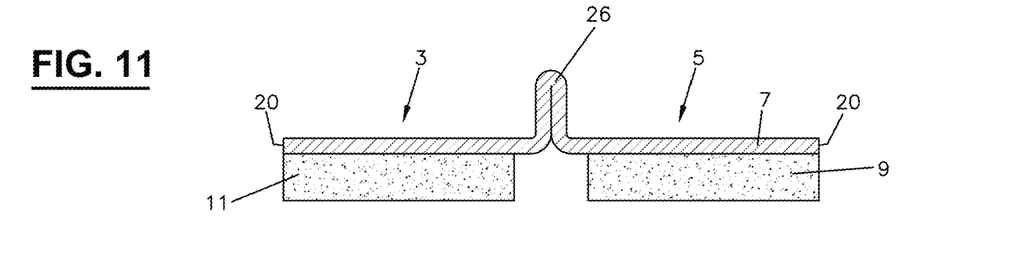
FIG. 11 applicator device with aligned borders.

In combination or as an alternative, i.e. in a layout where the weakening line is at least in the frontal section where the carrier sheet gets close to the surface to be treated identical with the contour with the rim of the pad, the thickness of the pad's material is chosen such that the contact of the carrier sheet with the surface to be treated is avoided (cf. FIG. 11). A sufficiently thick pad causes a spreading of the wings 3, 5 because of one or more of the following:

The material of the pads 9, 11 expands, i.e. increases its height. This effect may be supported by choosing a resilient material like a foam or a sponge, and by compressing the material when closing the applicator.

Once the applicator is opened, the grip is tweaked between fingers, pincers, or the like whereby as well a spreading force is generated.

The exact adaption of the weakening line in the carrier sheet to the contour of the pads 9, 11 is preferably made also in other parts, i.e. for at least 50%, preferably at least 80%, more preferably at least 90% of the total contour of the pad. (The limits are generally applicable to the execution examples.)

The thickness of the pads 9, 11 may be:

at most 10 mm, preferably at most 5 mm and most preferably at most 3 mm and at least 1 mm, preferably at least 2 mm, for a pad diameter up to 10 cm.

at most 20 mm, preferably at most 10 mm and most preferably at most 5 mm, and at least 3 mm, preferably at least 4 mm, for a pad diameter of at least 10 cm.

at most 1/10, preferably at most 1/20 and most preferably 1/30, and at least 1/50, more preferably at least 1/40 of the diameter of the pad.

From the foregoing it is obvious that the conformity between weakening line and pads is required where the pad is functionally a rim of the applicator once the part exterior to the weakening line is removed. It is particularly in these regions where during first contact of the applicator with a surface, the rim of the carrier sheet may get in contact with that surface before the pad.

In order to avoid irritations of the surface 36, the contour of the pads 9, 11 not adjacent to the grip portion, i.e. where their borders about coincide with the weakening line 14, 16, is substantially void of sharp angles, e.g. as illustrated about semi-circular. In general, the pads may have any shape with any bend in this section having a curvature radius not below a predetermined value. A suitable lower limit has been found to be 1/5 of the maximal distance of two points on the overall contour, although lower curvature radiiare applicable, e.g. down to 1/50 of that distance. In other terms, usable known geometric shapes are a part, in particular a half, of a circle, an ellipsis, an oval or other line shapes avoiding sharp angles.

An important aspect of the applicator 1 is the close conformity of the weakening line 14, 16 with the contour of the pad 9, 11. Therefore, producing the weakening lines 14, 16 requires high precision. It has been found that such precisely shaped weakening line 14, 16 can be produced expeditiously in using a laser.

The following materials have proven to be suited for the applicator 1:

Carrier sheet 7 (each time material and thickness in μm=Micrometer):

OPP(oriented polypropylene, thickness e.g. 30 μm, on PE, thickness 30 μm: soft appearance.

PET 12 μm, aluminium 8 μm, PE 100 μm—multilayer: Stiffer appearance;

PET 12 μm, aluminium 8.5 μm, PE 75 μm—multilayer;

PET 12 μm, aluminium 12 μm, PP 40 μm—multilayer.

(PE: polyethylene; PET: polyethylene-terephthalate; PP: polypropylene)

Pads 14, 16:

non-woven material, like fleece, felt;

woven and other fibrous material wherein fibres are linked; ("woven material" generally designates textile material or materials consisting substantially of fibres, where the fibres are interconnected, e.g. by a method known in the art as weaving, knitting, etc.

soft polymer material, like foam, sponge.

The applicator may have a size generally adapted to the field of use. For cosmetic use, sizes, i.e. maximal width of weakening line 14, 16 may be at least 1 cm up to several centimetres, e.g. up to 10 cm. Other e.g. technical applications may require sizes up to 50 cm as preferred size.

An issue consists in if the upper and lower wings 3, 5 readily spread as illustrated in FIG. 4. Once the part exterior to the weakening line 14, 16 is ripped off, the wings 3, 5 will already spread slightly, however probably not to an extent that they are perfectly spread to lay flat on a surface 36.

It has been found that a cut-out 41 about centrally in the grip portion 26 allows forcing the wings 3, 5 to spread further by moving the sections 43, 44 to the left and right of the cut-out 41 towards each other. Thereafter, further bending occurs while being laid on a surface 36 without the carrier sheet boundaries touching the surface (cf. FIG. 4).

Figure 5:
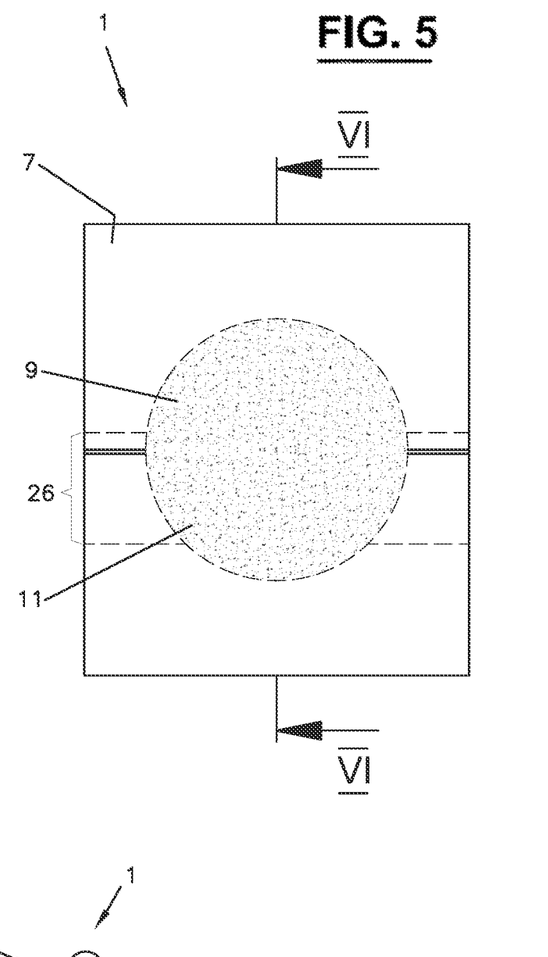
FIG. 5 intermediate production state of the applicator, with the handle produced and a pad placed.
Figure 6:
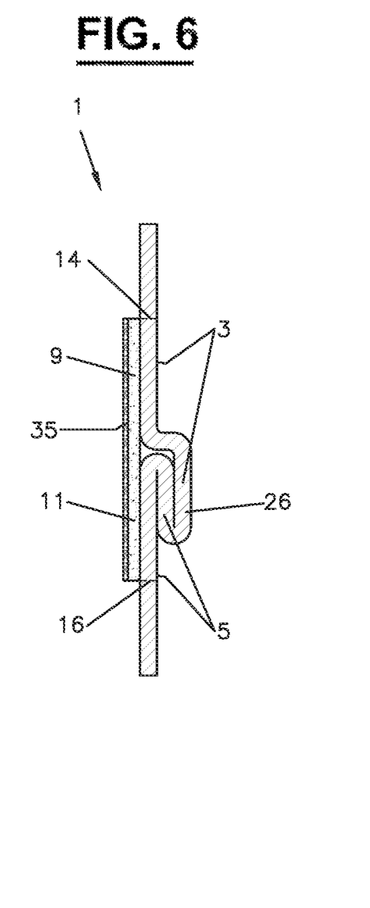
FIG. 6 cross-section according VI-VI in FIG. 5.
Figure 7:
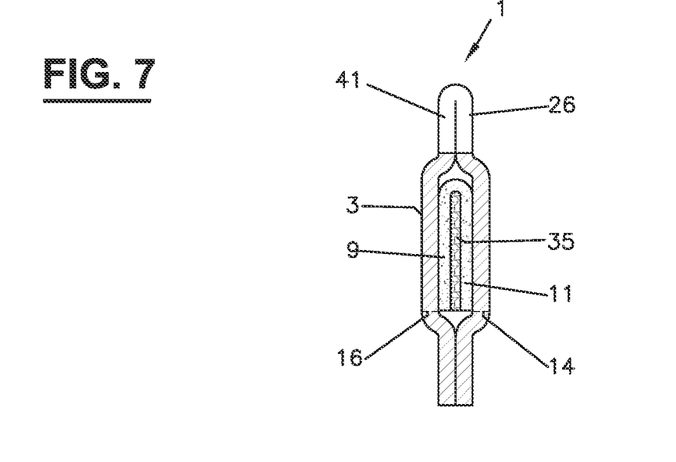
FIG. 7 cross-section of the applicator produced according to FIGS. 5 and 6.

FIGS. 5 to 6 show an alternative of producing the applicator device 1 and the resulting applicator ready for use. In a first step, the grip portion 26 is formed by folding upper and lower grip sections 30, 32 on each other and connecting them, e.g. by welding, gluing. The resulting intermediate arrangement is flattened, resulting in the configuration of FIGS. 5 and 6. A pad representing both pads 9, 11 as one uniform piece shaped according to the united weakening lines 14, 16 is placed within these weakening lines, and the agent is applied to the pad 9, 11. Or the pad as used for being placed has already been provided with the agent. The upper and lower wings 3, 5 are superposed and the seam is closed by a suitable technique like welding, gluing, resulting in the configuration shown in FIG. 7 as a cross-section.

$2^{nd}$ Example

Sometimes a device is required to apply an agent to a surface, e.g. the skin, yet a mechanical interaction with the surface is not required. Or the agent has such properties, that pads 9, 11 are not required or even disadvantageous.

Figure 8:
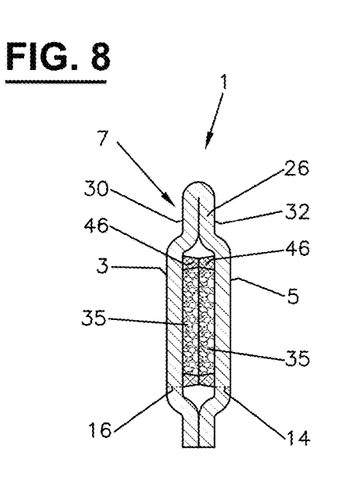
FIG. 8 a second embodiment of the applicator device; cross-section analogous to FIG. 2.
Figure 9:
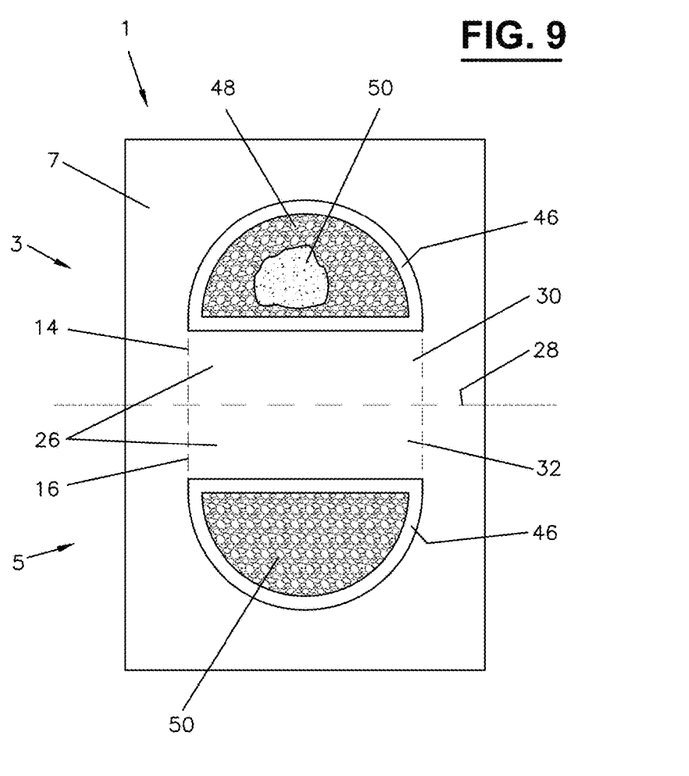
FIG. 9 top view on applicator device of FIG. 5 before folding and sealing.

A suitable applicator device 1 (cf. FIGS. 8-10) for such situations is provided with a rib 46 running along each weakening line 14, 16. Preferably the ends are closed so to form a basin 48 on the upper and lower wing 3, 5 of the carrier sheet 7. The interior of the basin 48 may be filled with the agent, either completely (cf. FIG. 8) or only partly, i.e. up to a level lower than the height of the rib 46. The basin 48 may contain a pad 50, too, of a material suited for pad 9, 11 of the first execution example. As the rib 46 is securing that the edge 20 of the carrier sheet 7 does not get in contact with the surface 36, the pad 50 arranged in the basin 48 may have any shape and may fill only a part of the basin 48. In particular, the pad 50 may merely have the function of sustainably releasing the agent. The pad 50 may be present on one or both (different from FIG. 9) wings, or be absent (FIG. 8). In some embodiments, the applicator sections are comprised of the rib 46 which is shaped as a linear elevation and configured to retain the agent within the applicator section.

The rib or retaining elevation 46 may be printed or otherwise applied to the carrier sheet 7. It consists preferably of a resilient material like silicon or another elastomer, a foam material, a fibre material, or a mixture thereof. Furthermore, particularly if a fibre material is used, it may be provided with repellent activity, e.g. for an agent disposed in water, it may be hydrophobic, or for an agent in oil, it may be lipophobic.

The height of the rib 46 depends in the size of the applicator, where the diameter of the rib 46 may be taken as the measure (cf. above in the first example for the definition of "diameter"). An excessively low rib is not capable to retain a sufficient amount of agent. An excessively high rib creates tensions while sealing the applicator outside the weakening lines which may cause to ripping open of the carrier sheet primarily along the weakening lines 14, 16. It has been found that a minimum rib height is 0.05 mm, with further possible heights of 0.1 mm, 0.5 mm, and 1 mm, the latter merely for greater applicators. Each time, the values may be considered lower limits. An upper limit has been found to be about 4 to 5 mm for the largest applicators (diameters of basin of 40 cm to 50 cm). Another approach which proved to be useful is the dimensioning in relation to the size of the applicator, more particular the diameter of the basins 48 created by the ribs 46: The rib height may be chosen in the range 0.5% to 2% of the diameter. E.g. the rib height for an applicator of basin diameter 5 cm may range from 0.25 mm to 1 mm, for diameter 1.5 cm from 0.075 mm to 0.3 mm, and for 40 cm diameter from 2 mm to 8 mm. From these numbers, it is evident that a tendency from higher values at lower diameter to lower values at larger diameter is observed. Of course, the properties of the agent and the requirements of the application are to be taken into account as well, e.g. the amount of the agent to be effective, its rheological properties, and the size of the area to be treated, to name some.

The applicator according to this embodiment may furthermore correspond in any other aspect to the first embodiment. In particular, the cut-out or notch 41 may be provided in order to allow a forced spreading of the wings in use as set forth above.

For this example, too, the recess may even be lower down to zero if the height of the elevation 46 is properly chosen. In particular, the same considerations and dimensions are applicable as set forth above for a weakening line at least partially exactly following the contour of pads 9, 10 with respect to FIG. 11.

Figure 10:
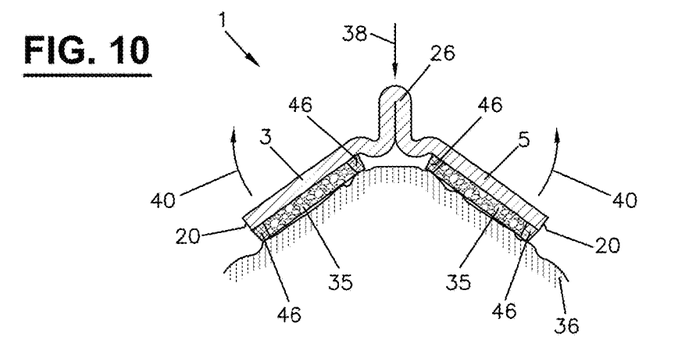
FIG. 10 illustration of use of the second embodiment analogous to FIG. 4.

As FIG. 10 illustrates, it is even possible to set the rim of the carrier sheet 7, i.e. the main weakening lines 14, 16, back with respect to the rim of the rib 46, provided that the rib is not or only weakly connected (glued, welded etc.) with the part of the carrier sheet outside the main weakening line, so that this part of the carrier sheet may be ripped off without damaging the rib 46. The distance by which the main weakening 14, 16 lines may be set back with respect to the rib is at most ½, preferably at most ¼ of the foot of the rib, i.e. the width of the rib measured where it touches the carrier sheet.

Field of Application

The applicator device described may be used to apply an agent to any surface and in particularly a sensible surface, e.g. parts of human skin. Further advantages are that neither the user gets in contact with an agent to be applied and contained in the applicator device, nor the surface to be treated needs to be touched. Until use, the agent which may be sensitive with respect to environmental influence, (air, temperature, or light) is tightly sealed, and by an appropriate design of the carrier sheet, in particular by the choice of its material, it is well protected against detrimental influences.

The applicator device is suited to be used for medical or cosmetic applications, in particular for applying an agent on or treating a portion of sensible skin, e.g. the perivulvar region, where it is a prominent advantage for hygienic or psychological reasons or even convenience not either to get in contact with the treated area or the agent. Professional users, like medicinal staff, need as well such devices to avoid contact with medical agents and sometimes also a contact with the skin of a patient.

As well, the applicator device may be used for treating delicate technical surfaces, where a contact of a supporting structure like the carrier sheet with the surface may irritate (scratch etc.) the surface or a contact of the user with the agent is to be avoided.

The applicator as described provides the general advantage that after opening, the working surface is instantly in a ready-for-use state, instead of the agent first to be squeezed out of a reservoir. Another advantage is the exactly predetermined amount of agent which is applied.

Another advantage is that in using high-precision methods for providing the weakening line, like laser-cutting, the weakening lines are precisely adapted to the contour of the active surface so that it is avoided that parts of the protective sheet extend beyond the active surface and thereby, it is avoided that the protective layer gets in contact with the surface to be treated, particularly during the phase where the wings of an applicator device are spread while approaching the surface.

Methods like laser-cutting even provide more liberty in designing the shape of the weakening lines. In particularly, the weakening lines can be designed in avoiding sharp corners so that the excess material rips off exactly along the weakening lines and is preferably eliminated. A further advantage of such a design is that the excess material of the protective sheet is ripped off in one single action. Thereby, the risk that the user gets unfortunately in contact with the agent is reduced in addition to attaining a faster opening of the applicator pad.

The agent bearing portion may comprise one of:
a volume (9, 11) of a material carrying the agent, or
a confinement structure (46) shaped as a linear elevation and configured to retain the agent within the applicator section,
wherein the weakening lines (14, 16) are recessed by a recess distance into the agent bearing portion (9, 11, 46),
wherein the weakening lines are parallel to the border of the agent bearing portion, the recess distance being at least 0.5 mm and at most 10 mm for an applicator device of a size up to 10 cm, and at least 1 mm and at most 20 mm for an applicator device of a size above 10 cm,
with the size of the applicator device being a maximal distance of two points of the border of applicator section, and
wherein when a confinement structure is present, the recess distance is additionally limited to at most 50% of a width of a linear elevation of the confinement structure at the confinement structure's contact surface to the carrier sheet (7), the carrier sheet being a flexible material.

The weakening lines (14, 16) may be one or more of:
sections having a lower limit of curvature radius not less than 1 mm,
sections having a lower limit of curvature radius not less than 1% of a maximal distance between two maximally distant points of the weakening lines; or
a section consisting of one of: a part of a circle, a part of an ellipsis, a part of an oval, or combinations thereof; and
wherein all transitions between any two sections comply with the lower limit of curvature radius and are continuous in case at least two sections are present.

A maximal distance between two maximally distant points of the weakening lines is at least 0.5 cm and at most 50 cm.

A width of the grip zone (26; 30, 32) is at least 5 mm.

The confinement structure (46) may comprise one or more of a non-woven fiber material, a woven material, a sponge, and a foam, for sustained application of the agent.

In some embodiments, the confinement structure (46) overlaps the weakening lines (14, 16) so that in using the applicator device on a surface (36), and with the excess material of the top layer and the bottom layers (3,5) being ripped off along the weakening lines, ripped-off edges of the top and bottom layer (3, 5) are kept apart from the surface to be treated by the confinement structure.

Figure 12:
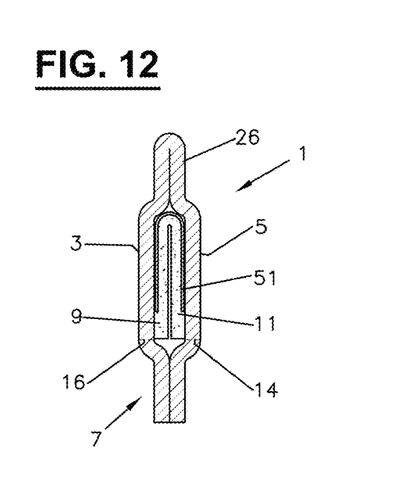
FIG. 12 section similar FIG. 7 through an applicator device with spring element for spreading.
Figure 13:
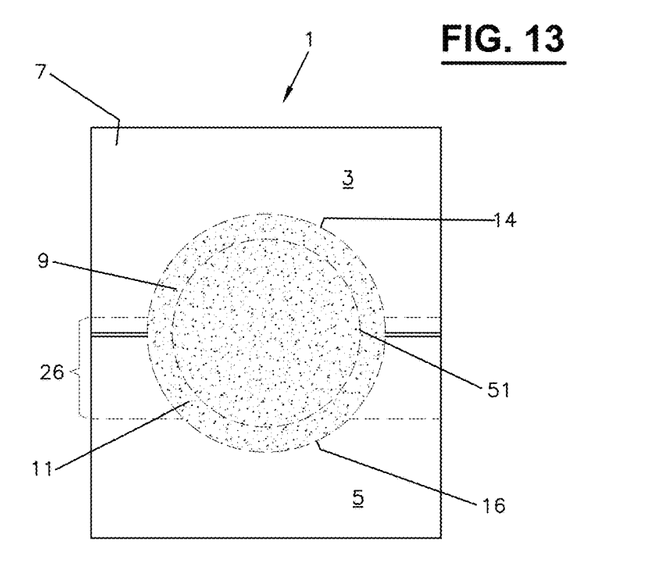
FIG. 13, 14 top view similar to FIG. 5 on applicators devices before folding and sealing with variants of a spring element.
Figure 14:
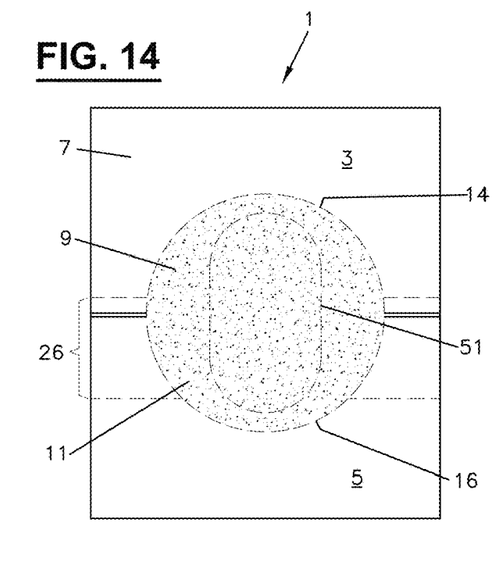
Figure 15:
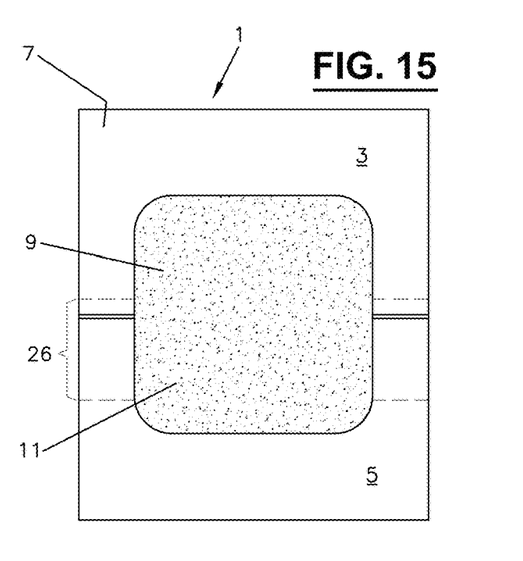
FIG. 15 top view as FIG. 5, different contour of pad and weakening line.

Based on the preceding description of preferred embodiments, the one skilled in the art is enabled to derive modifications and complements without leaving the scope of protection which is defined by the claims. Conceivable are the following variations:

- Upper and lower wings are separate individual sheets welded (or otherwise connected) at their grip portion, instead of being parts of one sheet and folded on each other.
- The grip section may be arranged between the wings 3, 5, or exterior sections, i.e terminal bottom and top sections of the sheet 7 as shown in FIG. 3, so that the wings 3, 5 are adjacent and separated be the fold line 28.
- The contour of the applicator 1 deviates from rectangular. Possible is e.g. polygonal, round or arbitrary shapes. Obviously such shapes may be derived from the illustration by cutting out the required contour. Almost unavoidably, the gripping portion will be delimited by an about straight line which constitutes the hinges for spreading the upper and lower wings.
- The material of the carrier sheet is selected to protect the agent and/or the pads 9, 11 against environmental influence, e.g. by a metal layer to render if impervious to gas and opaque.
- The carrier sheet consists of a quite stiff material, and a flexible, substantially strip shaped zone extends along the boundary between grip portion 26 and the movable part of upper and lower wings in order to constitute a hinge and allowing the wings to spread such a flexible zone may be a particularly thin material.
- The agent is applied on the surface, impregnated, or both to the pads 9, 11, and any shape and manner, e.g. like a drop, and in particularly not covering the whole surface of the pads or the basin as the illustrations show.
- The conformity of the main weakening line with the contour of the pads or the basin, where they are adjacent the border of the applicator once the excess part of the carrier sheet is ripped off along the weakening line, is understood to lay within the tolerance values known in the art.
- The strip-shaped grip portions are located at another border of the wings. However, it is supposed that they have to be designed mirror-symmetrically with respect to the fold line in order that they can be superposed. In particular, they may be arranged at the borders of the wings opposite the fold line 28, and the wings adjoin the fold line.
- For facilitating the spreading of the wings 3, 5, pads or flaps may be attached to their surface, e.g. by welding or gluing. An alternative consists in cutting tongues in the carrier sheet 7 within the wings 3, 5. E.g. a substantially U-shaped cut (or L-shaped, f.i.) may be applied by a laser large enough to be caught by fingers or a tool like a pincer. The portion of the pads 9, 11 below such a tongue should not be connected (glued) to the carrier sheet.
- A spring element 51 (cf. FIG. 12) may be embedded in the applicator device. The spring element may be a strip of an elastic material, like a polymer or a metal. The material has to be chosen to avoid detrimental effects. Generally, it needs to be inert with respect to the agent. However, a non-inert material may be coated by a protective layer. The spring element 51 is bent during closing the applicator 1 and tensioned thereby. Once the applicator is opened for use, the spring element 51 will spread the wings 3, 5. The use of the spring element 51 allows obtaining an immediate and predefined spreading of the wings. In particular, the spring element may be straight or angled in the relaxed state, so that after opening, the wings are moved to an about straight or aligned configuration or spread up to about the mentioned original angle of the spring element. It is not excluded that the spring element is positioned in the interstice between the pads 9, 11 (e.g. as an angled strip), or its ends are embedded in the pads 9, 11. In particular, it is conceivable that pads 9, 11 connected by the spring element (or with the spring element 51 embedded) are attached to the carrier sheet as a prefabricated unit. The fold or the bend of the U-shaped spring element 51 (cf. FIG. 12) may comprise or be constituted by one or more edges according to another variant. As a material of the spring element, polymeric material is preferred, in particular HDPE (high density polyethylene) or PET. It is preferably a disc having a thickness of up to 3 mm, preferably maximally 0.5 mm, and more preferably 0.1 mm. Other conceivable shapes are distorted disc like oval, elliptic, with the elongated direction traversing the grip 26, up to a strip of about rectangular shape.
- The shape of the weakening line and of the contour of the pads may be varied broadly. In view of an optimal use of the relatively expensive material of the pads 9, 11, approaching a rectangular shape or another shape, e.g. hexagonal, which allow placing a number of pads on a plane with few or no material unused, i.e. a low loss, is preferred. In view of a rapid, exact and safe detaching of excess carrier sheet material along the weakening lines, corners in the course of the weakening need to be not too sharp. It has been found that the corners need to be rounded by a radius of at least 1 mm in order that the ripping follows the weakening lines.
- The pads 7, 9, or at least one of them, consist of a resilient compressible material, and the total thickness in expanded state of the pads exceeds the available space within the closed applicator (shown e.g. in FIGS. 2 and 7). Once the applicator is opened, the compressed material expands. By this increase of its volume, the wings of the applicator are spread. Suitable preferred materials are polyurethane foams, in particular polyurethane foams based on toluene diisocyanate. This type of polyurethane has low density and a low volume expansion. The absorption rate may be selected in view of the intended use and required high or low loading of the agent bearing section with an agent.

The invention claimed is:

1. An applicator device (1) for applying an agent (35) to a delicate surface (36), the applicator device (1) comprising:
   a carrier sheet (7) defining a top layer (3) and a bottom layer (5) of the applicator device (1);

a grip zone (26) joining together an edge of each of the top layer (3) and the bottom layer (5);
parallel weakening lines (14, 16) extending within the top and the bottom layers (3, 5) starting and ending at the grip zone; and
an applicator section (9, 11, 46) located on an interior side of the top and bottom layers (3, 5), the applicator section being defined by the parallel weakening lines,
the agent being borne on an agent bearing portion located on the applicator section on the interior side of at least one of the top and bottom layers (3, 5),
wherein when the agent bearing portion is arranged on the interior side of both of the top and bottom layers, a first part of the agent bearing portion on the interior side of the top layer is mirror-shaped to a second part of the agent bearing portion on the interior side of the bottom layer so borders of the first and second parts of the agent bearing portion coincide,
the parallel weakening lines being surrounded by excess material of the top and bottom layers (3, 5) connected with each other to constitute a sealing around the first and second applicator pads (9, 11), the excess material of the top layer and the bottom layer (3, 5) being configured to be ripped off along the weakening lines,
wherein a border of the applicator section (9, 11, 46) is recessed with respect to a border of the agent bearing portion,
the agent bearing portion comprising one of:
a volume (9, 11) of a material carrying the agent, or
a confinement structure (46) shaped as a linear elevation and configured to retain the agent within the applicator section,
wherein the weakening lines (14, 16) are recessed by a recess distance into the agent bearing portion (9, 11, 46),
wherein the weakening lines are parallel to the border of the agent bearing portion,
the recess distance being at least 0.5 mm and at most 10 mm for an applicator device of a size up to 10 cm, and at least 1 mm and at most 20 mm for an applicator device of a size above 10 cm,
with the size of the applicator device being a maximal distance of two points of the border of applicator section, and
wherein when a confinement structure is present, the recess distance is additionally limited to at most 50% of a width of a linear elevation of the confinement structure at the confinement structure's contact surface to the carrier sheet (7), the carrier sheet being a flexible material.

2. The applicator device (1) according to claim 1, wherein the weakening lines (14, 16) consist of one or more of:
sections having a lower limit of curvature radius not less than 1 mm,
sections having a lower limit of curvature radius not less than 1% of a maximal distance between two maximally distant points of the weakening lines; or
a section consisting of one of: a part of a circle, a part of an ellipsis, a part of an oval, or combinations thereof; and
wherein all transitions between any two sections comply with the lower limit of curvature radius and are continuous in case at least two sections are present.

3. The applicator device (1) according to claim 1, wherein a maximal distance between two maximally distant points of the weakening lines is at least 0.5 cm and at most 50 cm.

4. The applicator device (1) according to claim 1, wherein a width of the grip zone (26; 30, 32) is at least 5 mm.

5. The applicator device (1) according to claim 1, wherein the confinement structure (46) comprises one or more of a non-woven fiber material, a woven material, a sponge, and a foam, for sustained application of the agent.

6. The applicator device (1) according to claim 1, wherein the confinement structure (46) overlaps the weakening lines (14, 16) so that in using the applicator device on a surface (36), and with the excess material of the top layer and the bottom layer (3, 5) being ripped off along the weakening lines, ripped-off edges of the top and bottom layer (3, 5) are kept apart from the surface to be treated by the confinement structure.

7. The applicator device (1) according to claim 1, wherein a height of the volume (9, 11) carrying the agent or a height of the confinement structure (46), at least portions of a rim of the confinement structure (46) furthest distant from the grip zone (26) and constituting at least 50% of an overall perimeter of the volume carrying the agent or the confinement structure, is one of:
at most 10 mm, and at least an effective height, for the volume carrying the agent or the confinement structure having a diameter of less than 10 cm;
at most 20 mm, and at least an effective height, for the volume carrying the agent or the confinement structure having a diameter of at least 10 cm;
at most 1/10, and at least 1/50, of the volume carrying the agent or the confinement structure.

8. The applicator device (1) according to claim 1, wherein the agent confinement structure comprises a resilient polymeric material, shaped as a rib (46) interior to and along the weakening lines (14, 16).

9. The applicator device (1) according to claim 8, wherein a height of the rib (46) is selected such that contact of an edge of the applicator section is from 0.5% to 2% of a diameter of the confinement structure (46), the diameter being the largest distance of two points of a linear elevation of the confinement structure.

10. The applicator device (1) according to claim 1, wherein the top and bottom layers (3, 5) are attached to each other exterior to the applicator section, so that the agent (35) is confined within the applicator section.

11. The applicator device (1) according to claim 1, wherein the top and bottom layers (3, 5) comprise a compound material comprising at least two sub-layers, where at least one sub-layer comprises a polymeric material.

12. The applicator device (1) according to claim 1, wherein the top and bottom layers (3, 5) are constituted by a one-piece sheet folded on itself along an edge of the grip zone (26).

13. The applicator device (1) according to claim 1, wherein the portion of the volume (9, 11) carrying the agent comprises a resiliently compressible material of a thickness that such that the resiliently compressible material is compressed in a closed state of the applicator device, so that after ripping off the excess material along the weakening lines, the compressible material tends to expand whereby the bottom layer and the top layer are spread from each other.

14. The applicator device (1) according to claim 1, wherein a two-dimensional, resiliently bendable spring element is present and extends in a bent, tensioned state between the top (3) and bottom (5) layers in such an arrangement that the resiliently bendable spring element exerts a force on the top layer (3) and bottom layer (5) tending to increase the distance between the top and bottom layers.

15. The applicator device (1) according to claim 1, wherein the grip zone (26) includes at least one notch (41) located at an edge of a top portion of the grip zone and extending from the edge of the top portion of the grip zone toward an opposed limitation of the grip zone where the grip zone joins together the edge of each of the top layer (3) and the bottom layer (5), the at least one notch (41) being provided so that the grip zone may be bent to create a force on the top and bottom layers (3, 5) to spread effectively the top layer apart from the bottom layer.

16. The applicator device (1) according to claim 1, wherein the agent is the one or more of a cosmetic, a medical effective agent, and a pharmaceutically effective agent.

17. An applicator device (1) for applying an agent (35) to a delicate surface (36), the applicator device (1) comprising:
a carrier sheet (7) defining a top layer (3) and a bottom layer (5) of the applicator device (1);
a grip zone (26) joining together an edge of each of the top layer (3) and the bottom layer (5);
parallel weakening lines (14, 16) extending within the top and the bottom layers (3, 5) starting and ending at the grip zone; and
an applicator section (9, 11, 46) located on an interior side of the top and bottom layers (3, 5), the applicator section being defined by the parallel weakening lines,
the agent being borne on an agent bearing portion located on the applicator section on the interior side of at least one of the top and bottom layers (3, 5),
wherein when the agent bearing portion is arranged on the interior side of both of the top and bottom layers, a first part of the agent bearing portion on the interior side of the top layer is mirror-shaped to a second part of the agent bearing portion on the interior side of the bottom layer so borders of the first and second parts of the agent bearing portion coincide,
the parallel weakening lines being surrounded by excess material of the top and bottom layers (3, 5) connected with each other to constitute a sealing around the first and second applicator pads (9, 11), the excess material of the top layer and the bottom layer (3, 5) being configured to be ripped off along the weakening lines,
wherein a border of the applicator section (9, 11, 46) is coincident with or is recessed with respect to a border of the agent bearing portion,
the agent bearing portion comprising a volume (9, 11) of a material carrying the agent,
wherein the portion of the volume (9, 11) carrying the agent comprises a resiliently compressible material of a thickness such that the resiliently compressible material is compressed in a closed state of the applicator device, so that after ripping off the excess material along the weakening lines, the compressible material tends to expand whereby the bottom layer and the top layer are spread from each other.

18. An applicator device (1) for applying an agent (35) to a delicate surface (36), the applicator device (1) comprising:
a carrier sheet (7) defining a top layer (3) and a bottom layer (5) of the applicator device (1);
a grip zone (26) joining together an edge of each of the top layer (3) and the bottom layer (5);
parallel weakening lines (14, 16) extending within the top and the bottom layers (3, 5) starting and ending at the grip zone; and
an applicator section (9, 11, 46) located on an interior side of the top and bottom layers (3, 5), the applicator section being defined by the parallel weakening lines,
the agent being borne on an agent bearing portion located on the applicator section on the interior side of at least one of the top and bottom layers (3, 5),
wherein when the agent bearing portion is arranged on the interior side of both of the top and bottom layers, a first part of the agent bearing portion on the interior side of the top layer is mirror-shaped to a second part of the agent bearing portion on the interior side of the bottom layer so borders of the first and second parts of the agent bearing portion coincide,
the parallel weakening lines being surrounded by excess material of the top and bottom layers (3, 5) connected with each other to constitute a sealing around the first and second applicator pads (9, 11), the excess material of the top layer and the bottom layer (3, 5) being configured to be ripped off along the weakening lines,
wherein a border of the applicator section (9, 11, 46) is coincident with or is recessed with respect to a border of the agent bearing portion,
the agent bearing portion comprising one of:
a volume (9, 11) of a material carrying the agent, or
a confinement structure (46) shaped as a linear elevation and configured to retain the agent within the applicator section,
wherein a two-dimensional, resiliently bendable spring element is present and extends in a bent, tensioned state between the top (3) and bottom (5) layers in such an arrangement that the resiliently bendable spring element exerts a force on the top layer (3) and bottom layer (5) tending to increase the distance between the top and bottom layers.

19. An applicator device (1) for applying an agent (35) to a delicate surface (36), the applicator device (1) comprising:
a carrier sheet (7) defining a top layer (3) and a bottom layer (5) of the applicator device (1);
a grip zone (26) joining together an edge of each of the top layer (3) and the bottom layer (5);
parallel weakening lines (14, 16) extending within the top and the bottom layers (3, 5) starting and ending at the grip zone; and
an applicator section (9, 11, 46) located on an interior side of the top and bottom layers (3, 5), the applicator section being defined by the parallel weakening lines,
the agent being borne on an agent bearing portion located on the applicator section on the interior side of at least one of the top and bottom layers (3, 5),
wherein when the agent bearing portion is arranged on the interior side of both of the top and bottom layers, a first part of the agent bearing portion on the interior side of the top layer is mirror-shaped to a second part of the agent bearing portion on the interior side of the bottom layer so borders of the first and second parts of the agent bearing portion coincide,
the parallel weakening lines being surrounded by excess material of the top and bottom layers (3, 5) connected with each other to constitute a sealing around the first and second applicator pads (9, 11), the excess material of the top layer and the bottom layer (3, 5) being configured to be ripped off along the weakening lines,
wherein a border of the applicator section (9, 11, 46) is coincident with or is recessed with respect to a border of the agent bearing portion,
the agent bearing portion comprising one of:
a volume (9, 11) of a material carrying the agent, or
a confinement structure (46) shaped as a linear elevation and configured to retain the agent within the applicator section, wherein the grip zone (26) includes at least one notch (41) located at an edge of a top portion of the grip zone and extending from the edge of the top portion of the grip zone toward an opposed limitation of the grip zone where the grip zone joins together the edge of each of the top layer (3) and the bottom layer (5), the at least one notch (41) being provided so that the grip zone may be bent to create a force on the top and bottom layers (3, 5) to spread effectively the top layer apart from the bottom layer.

\* \* \* \* \*